(12) United States Patent
Datta (10) Patent No.: US 11,224,482 B2
(45) Date of Patent: Jan. 18, 2022

(54) CATHETER HAVING TWO-PIECE CONNECTOR FOR A SPLIT HANDLE ASSEMBLY

(71) Applicant: BIOSENSE WEBSTER (ISRAEL) LTD., Yokneam (IL)

(72) Inventor: Keshava Datta, Chino Hills, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 326 days.

(21) Appl. No.: 16/416,636

(22) Filed: May 20, 2019

(65) Prior Publication Data
US 2019/0269458 A1 Sep. 5, 2019

Related U.S. Application Data

(62) Division of application No. 15/259,020, filed on Sep. 7, 2016, now Pat. No. 10,292,764, which is a division
(Continued)

(51) Int. Cl.
*A61B 18/14* (2006.01)
*A61B 5/287* (2021.01)
(Continued)

(52) U.S. Cl.
CPC ............ *A61B 18/1492* (2013.01); *A61B 5/02* (2013.01); *A61B 5/287* (2021.01); *A61B 5/6852* (2013.01);
(Continued)

(58) Field of Classification Search
CPC ... A61B 18/1492; A61B 5/287; A61B 5/6852; A61B 5/02; A61B 2018/00178;
(Continued)

(56) References Cited

U.S. PATENT DOCUMENTS 4,458,220 A 7/1984 Carter et al.
5,338,227 A 8/1994 Nakamura
(Continued)

FOREIGN PATENT DOCUMENTS

CN 1221519 A 6/1999
CN 101623195 A 1/2010
(Continued)

OTHER PUBLICATIONS

Australian Patent Office Examination Report No. 1 for Application No. 2013256142, dated Oct. 17, 2016, 3 pages.
(Continued)

*Primary Examiner* — Michael W Kahelin
(74) *Attorney, Agent, or Firm* — Etan S. Chatlynne; Roberts Calderon Safran & Cole P.C.

(57) ABSTRACT

A catheter and method for the treatment of a patient having atrial flutter or other arrhythmia comprises an elongated catheter body having an outer wall, proximal and distal ends, and at least one lumen extending therethrough. Further it has a distal tip section comprising a flexible tubing having a proximal end and a distal end and a plurality of lumens extending therethrough. The proximal end of the tip section is fixedly attached to the distal end of the catheter body. The tip section further comprises a nitinol tube having slots formed therein which causes the distal tip section to deflect using the same puller-wire action used to cause the deflectable catheter to deflect at a point proximal to the distal tip section.

17 Claims, 4 Drawing Sheets

Related U.S. Application Data of application No. 13/874,710, filed on May 1, 2013, now abandoned.

(60) Provisional application No. 61/642,582, filed on May 4, 2012.

(51) Int. Cl.

| | |
|---|---|
| *H01R 24/00* | (2011.01) |
| *A61B 5/02* | (2006.01) |
| *A61B 5/00* | (2006.01) |
| *H01R 13/506* | (2006.01) |
| *H01R 13/633* | (2006.01) |
| *H01R 13/64* | (2006.01) |
| *H01R 13/66* | (2006.01) |
| *A61B 18/00* | (2006.01) |

(52) U.S. Cl.
CPC .... *H01R 24/00* (2013.01); *A61B 2018/00178* (2013.01); *A61B 2018/00351* (2013.01); *A61B 2018/00434* (2013.01); *A61B 2018/00511* (2013.01); *A61B 2018/00577* (2013.01); *H01R 13/506* (2013.01); *H01R 13/633* (2013.01); *H01R 13/64* (2013.01); *H01R 13/6658* (2013.01); *H01R 2201/12* (2013.01)

(58) Field of Classification Search
CPC .. H01R 24/00; H01R 2201/12; H01R 13/506; H01R 13/633; H01R 13/64
See application file for complete search history.

(56) References Cited

U.S. PATENT DOCUMENTS

| | | | |
|---|---|---|---|
| 5,391,199 | A | 2/1995 | Ben-Haim |
| 5,405,269 | A | 4/1995 | Stupecky |
| 5,643,255 | A | 7/1997 | Organ |
| 5,697,909 | A | 12/1997 | Eggers et al. |
| 5,725,525 | A * | 3/1998 | Kordis ............... A61B 5/6858 606/41 |
| 5,743,903 | A | 4/1998 | Stern et al. |
| 5,991,355 | A | 11/1999 | Dahlke |
| 6,053,172 | A | 4/2000 | Hovda et al. |
| 6,062,902 | A | 5/2000 | Buckles et al. |
| 6,139,350 | A | 10/2000 | Mathesius |
| 6,239,724 | B1 | 5/2001 | Doron et al. |
| 6,332,089 | B1 | 12/2001 | Acker et al. |
| 6,419,515 | B1 | 7/2002 | Okayasu |
| 6,484,118 | B1 | 11/2002 | Govari |
| 6,618,612 | B1 | 9/2003 | Acker et al. |
| 6,690,963 | B2 | 2/2004 | Ben-Haim et al. |
| 6,817,884 | B1 | 11/2004 | Chen et al. |
| 6,857,904 | B2 | 2/2005 | Lai |
| 6,991,483 | B1 | 1/2006 | Milan et al. |
| 7,347,710 | B2 | 3/2008 | Ohtaka et al. |
| 7,481,664 | B1 | 1/2009 | Knoll et al. |
| 7,614,913 | B2 | 11/2009 | Ice |
| 7,860,553 | B2 | 12/2010 | Govari et al. |
| 8,043,106 | B1 | 10/2011 | Morello et al. |
| 2002/0065455 | A1 | 5/2002 | Ben-Haim et al. |
| 2002/0068930 | A1 | 6/2002 | Tasto et al. |
| 2003/0109778 | A1 | 6/2003 | Rashidi |
| 2003/0120150 | A1 | 6/2003 | Govari |
| 2004/0068178 | A1 | 4/2004 | Govari |
| 2004/0082866 | A1 | 4/2004 | Mott et al. |
| 2008/0306380 | A1 | 12/2008 | Parchak et al. |
| 2011/0098601 | A1 | 4/2011 | Huynh et al. |
| 2012/0095362 | A1 | 4/2012 | Fang et al. |

FOREIGN PATENT DOCUMENTS

| | | |
|---|---|---|
| CN | 201656165 U | 11/2010 |
| EP | 1169974 A1 | 1/2002 |
| JP | S5814476 A | 1/1983 |
| JP | H08511438 A | 12/1996 |
| JP | H09501328 A | 2/1997 |
| JP | 2000506027 A | 5/2000 |
| JP | 2001224556 A | 8/2001 |
| JP | 2002282361 A | 10/2002 |
| JP | 2006504473 A | 2/2006 |
| JP | 2007222617 A | 9/2007 |
| JP | 2010017549 A | 1/2010 |
| JP | 2010142648 A | 7/2010 |
| WO | 9605768 A1 | 2/1996 |
| WO | 9636282 A2 | 11/1996 |
| WO | 9819611 A1 | 5/1998 |
| WO | 9940856 A1 | 8/1999 |
| WO | 0071043 A1 | 11/2000 |
| WO | 0128446 A1 | 4/2001 |
| WO | 0136017 A2 | 5/2001 |
| WO | 2006055733 A1 | 5/2006 |
| WO | 2011114957 A1 | 9/2011 |
| WO | 2012019231 A1 | 2/2012 |

OTHER PUBLICATIONS

International Search Report for International Application No. PCT/US2013/039485, dated Aug. 22, 2013, 5 pages.
Japanese Decision of Refusal issued in Japanese Application No. 2015-510484, dated Mar. 20, 2018, 3 pages.
Japanese Notification of Reasons for Refusal issued in Japanese Application No. 2015-510484, dated Jan. 31, 2017, 7 pages.
Japanese Notification of Reasons for Refusal issued in Japanese Application No. 2015-510484, dated Sep. 19, 2017, 7 pages.
Office Action for Chinese Application No. 201380023468.6, dated Aug. 2, 2016, 5 pages.
Second Office Action for Chinese Application No. 201380023468.6, dated Mar. 9, 2017, 3 pages.
Third Office Action for Chinese Application No. 201380023468.6, dated Dec. 4, 2017, 3 pages.
Written Opinion for International Application No. PCT/US2013/039485, dated Nov. 4, 2014, 4 pages.
Extended European Search Report for European Application No. EP 20215409.2, dated May 11, 2021, 7 pages.

* cited by examiner

CATHETER HAVING TWO-PIECE CONNECTOR FOR A SPLIT HANDLE ASSEMBLY

CROSS-REFERENCE TO RELATED APPLICATION

The present application is a Divisional under 35 U.S.C. § 121 of U.S. patent application Ser. No. 15/259,020, filed Sep. 7, 2016, which is a Divisional under 35 U.S.C. § 121 of U.S. patent application Ser. No. 13/874,710, filed May 1, 2013, now abandoned, which claims the benefit of U.S. Provisional Patent Application No. 61/642,582, filed May 4, 2012. The entire contents these applications are incorporated by reference herein in their entirety.

FIELD OF INVENTION

The present invention relates to devices such as catheters for the diagnosis and/or treatment of cardiac arrhythmias, such as atrial fibrillation and atrial flutter. In particular the catheter has a two-piece connector for a split handle assembly to provide a means for more easily reusing and reprocessing various portions of the catheter assembly. The catheter handle assembly may also be used for other catheters such as renal ablation catheters.

BACKGROUND OF INVENTION

Cardiac arrhythmias, such as atrial flutter and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrhythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self-propagating. Alternatively, or in addition to the multiwavelet reentrant type, cardiac arrhythmias may also have a focal origin, such as when an isolated region of tissue in an atrium fires autonomously in a rapid, repetitive fashion. Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

Another type of arrhythmia is atrial flutter (AFL). Atrial flutter is an abnormal heart rhythm that occurs in the atria of the heart. When it first occurs, it is usually associated with a tachycardia and falls into the category of supra-ventricular tachycardia (SVT). While this rhythm occurs most often in individuals with cardiovascular disease or diabetes it may occur spontaneously in people with otherwise normal hearts. It is typically not a stable rhythm, and frequently degenerates into atrial fibrillation (AF). Therefore, treatment of AFL is desirable. Because of the reentrant nature of atrial flutter, it is often possible to ablate the circuit that causes atrial flutter. This is done in the electrophysiology lab by causing a ridge of scar tissue that crosses the path of the circuit that causes atrial flutter. Ablation of the isthmus, as discussed above, is a common treatment for typical atrial flutter. Physicians now a day utilized tip electrodes perpendicular to the tissue during flutter cases and drag the tip over the tissue to ablate linearly, this invention will allowed the physician to position the tip electrode parallel over the tissue with a single pulling action.

Atrial fibrillation occurs when the normal electrical impulses generated by the sinoatrial node are overwhelmed by disorganized electrical impulses that originate in the atria and pulmonary veins causing irregular impulses to be conducted to the ventricles. An irregular heartbeat results and may last from minutes to weeks, or even years. Atrial fibrillation (AF) is often a chronic condition that leads to a small increase in the risk of death often due to strokes. Risk increases with age. Approximately 8% of people over 80 having some amount of AF. Atrial fibrillation is often asymptomatic and is not in itself generally life-threatening, but it may result in palpitations, weakness, fainting, chest pain and congestive heart failure. Stroke risk increases during AF because blood may pool and form clots in the poorly contracting atria and the left atrial appendage. The first line of treatment for AF is medication that either slows the heart rate or revert the heart rhythm back to normal. Additionally, persons with AF are often given anticoagulants to protect them from the risk of stroke. The use of such anticoagulants comes with its own risk of internal bleeding. In some patients, medication is not sufficient and their AF is deemed to be drug-refractory, i.e., untreatable with standard pharmacological interventions. Synchronized electrical cardioversion may also be used to convert AF to a normal heart rhythm. Alternatively, AF patients are treated by catheter ablation. Such ablation is not successful in all patients, however. Thus, there is a need to have an alternative treatment for such patients. Surgical ablation is one option but also has additional risks traditionally associated with surgery.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having a tip electrode at its distal end into a heart chamber. A reference electrode is provided, generally taped to the skin of the patient or by means of a second catheter that is positioned in or near the heart. RF (radio frequency) current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60 degrees C., a thin transparent coating of dehydrated blood protein can form on the surface of the electrode. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs and the catheter must be removed from the body and the tip electrode cleaned.

Electrophysiology catheters used in mapping and ablation procedures are often connected to electroanatomic mapping systems such as the Carto 3® system from Biosense Webster, Inc. Electroanatomic mapping systems are used in conjunction with mapping catheters to determine the anatomy of the endocardial tissue in the heart and where nerve fibers, nodes and bundles appear on that tissue which may be ablated to treat the aforementioned cardiac arrhythmias. U.S. Pat. No. 7,860,553 discloses one such catheter connected to an electroanatomic mapping and/or ablation system the probe connects via a suitable mating connector to an adapter, which in turn connects, via another mating connector, to a console. The probe comprises a sensor and a probe microcircuit, which stores sensor calibration data. The adapter comprises a signal processing circuit for processing a signal that is output by the sensor. The adapter comprises its own microcircuit, which stores calibration data with respect to the signal processing circuit. A microcontroller in the adapter computes combined calibration data based on the data from both of the microcircuits. Signal analysis circuitry in the console receives the processed signal and analyzes this signal using the combined calibration data provided by the probe adapter. U.S. Patent Application No. 2008/0306380 discloses another such catheter and system where a probe adaptor having shielding is used to connect a probe such as a catheter to a console such as an electroanatomic mapping system.

The handles of electrophysiology catheters for the mapping and ablation of cardiac tissue contain electronic circuitry which converts signals from the tip or ring electrodes near the distal end of the catheter into digital signals that can be communicated to such electroanatomic mapping systems (such as the Carto 3® system from Biosense Webster) and/or an RF generator/ablation system. An electrical connection between the handle and such systems is necessary. This electrical connection is usually accomplished by a "male/female" pin-socket connector such as a Redel™ type connector or other such connector.

Primarily, these types of catheters are sold as single use only devices due to concerns with the ability to properly clean and sterilize the devices for reuse in addition to concerns that certain electronic circuitry in the devices may be damaged during reprocessing and make such devices less reliable in subsequent reuses.

There is increased desire to reuse electrophysiology catheters and/or components thereof. A catheter having a design that would facilitate such reuse would be desirable.

SUMMARY OF THE INVENTION

The present invention is directed to a catheter having a split-handle with a two piece connector that facilities reuse of a portion of the catheter assembly. Electronic circuitry that was typically placed in the operator controlled handle of the device has been moved to a two-piece connector so that the electronic circuitry may be separated from the operator controlled handle for ease of reprocessing. Additionally the two-piece connector for the split-handle design facilities placement of various electrical components in various portions of the connector for flexible design of reprocessed catheters, reuse of various components, EMI shielding and other purposes. Further, the connector design of the present invention provides for each of use with a keyed design and latching mechanisms to secure the pieces together and insure a proper connection.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
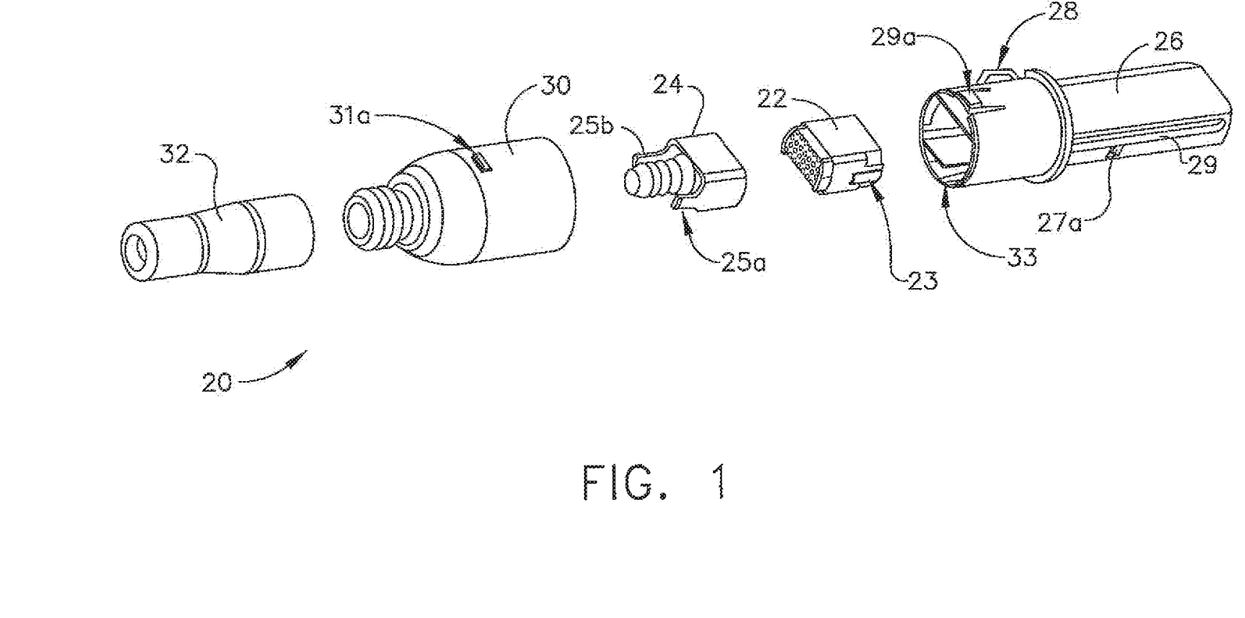
FIG. 1 is an exploded perspective view of the components that comprise the plug port assembly of the two-piece connector.

This invention shown and described herein relates to a catheter having a split handle, i.e. some of the components primarily the printed circuit board (PCB) and associated electronics that would have resided in the operational handle of prior catheter designs are moved to reside in one portion of the two-piece connector. FIG. 1 depicts an exploded perspective view of the components of plug assembly 20, a first portion of the two-piece connector. Plug assembly 20 comprises plug insulator 22. Contacts are inserted and held in plug insulator 22 which is designed to hold both pin or socket contacts making plug insulator 22 bi-gender. Plug insulator has sufficient longitudinal length so that contacts do not protrude beyond the front face of the plug insulator 22. Also, there is a first key 23 and second key on the opposite side (not shown) of different sizes which causes plug insulator to be keyed for one way insertion into the later described plug body 26. Insulator lead 24 is designed to capture and hold the plug insulator 22 through two snap features 25a and 25b. Plug body 26 is the main interface from the plug assembly 20 to the receptacle assembly 40. The plug insulator 22 and insulator lead 24 are held in place in plug body 26 when the snap features 25a and 25b are received in snap receivers 27a and 27b (shown in FIG. 4 and disposed opposite 27a). Plug body 26 also contains the lock and release button 28 and snap features. Lock and release button 28 engages and disengage the locking mechanism between plug assembly 20 and receptacle assembly 40. EEPROM recess 33 in body 26 facilitates placement and securing of an EEPROM in the plug assembly. Plug housing 30 captures the plug body 26 when snap features 29a and 29b (not shown) of plug body 26 engage with snap receivers 31a and 31b (not shown but disposed opposite 31a) in the plug housing 30. Plug housing 30 is the main part of the plug assembly 20 that is visible to the user when plug assembly 20 is connected to receptacle assembly 40. Strain relief 32 is used to create a transition from the plug housing 30 to the cable 15 and cable insulation 16 (depicted in FIGS. 3 and 4). The strain relief shown in FIG. 1 is the cable strain relief. The catheter variant is the same on the connector side and smaller on the catheter side.

Figure 2:
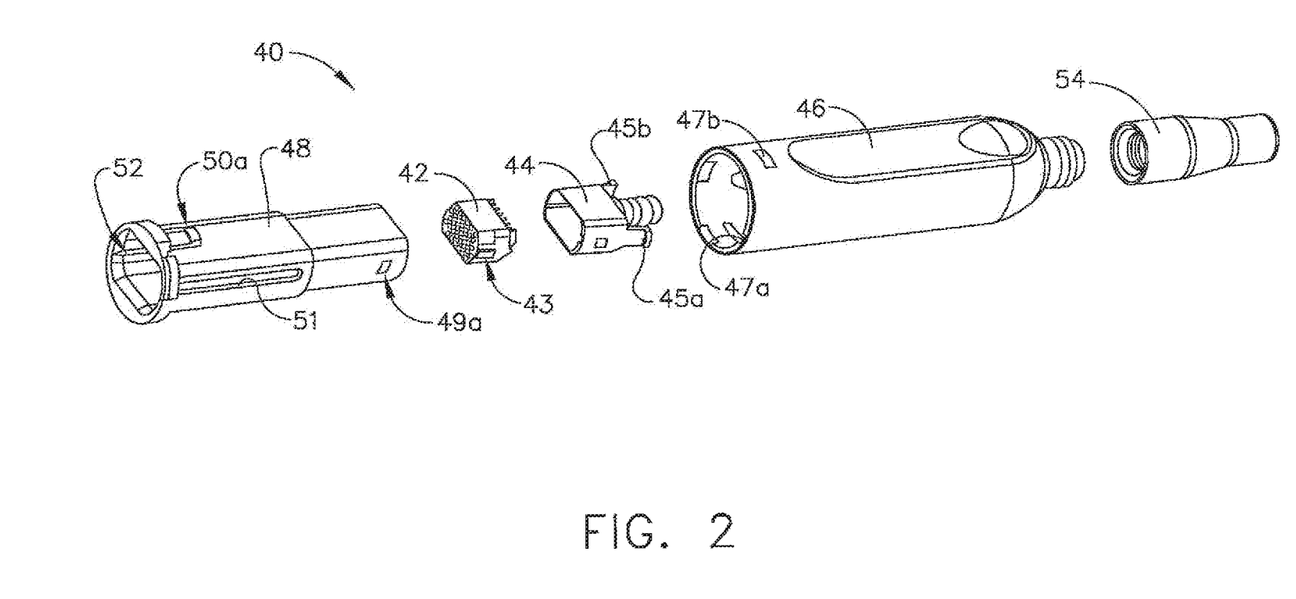
FIG. 2 is an exploded perspective view of the components that comprise the receptacle assembly of the two-piece connector.

FIG. 2 depicts an exploded perspective view of the receptacle assembly 40 of the present invention. Receptacle insulator 42 is designed to hold both pin or socket contacts making it bi-gender. Contacts are insert and held in place by the insulator lead 44. Because receptacle insulator 42 is shorter along its longitudinal axis than its companion plug insulator 22 the contacts will always protrude beyond the front face. Also, there is a first key 43 and second key on the opposite side (not shown) of different sizes which causes receptacle insulator to be keyed for one way insertion into the later described receptacle housing component. Insulator lead 44 is designed to capture and hold the receptacle insulator 42 when snap features 45a and 45b are engaged in the snap receivers 49a (shown) and 49b (not shown). Insulator lead 44 in the receptacle assembly can be substantially identical or identical to insulator lead 24 in the plug assembly to reduce component count although this is not necessary. Receptacle body 48 is the external portion of the interface from the plug assembly 20 to the receptacle assembly 40. Snap features 50a (shown) and 50b (not shown) are received by a further set of snap receivers 47a and 47b which reside in receptacle housing 46. Receptacle body 48 also includes the locking button catch feature 52 which holds the button during engagement and completes the lock between plug and receptacle assemblies. Receptacle housing 46 captures the receptacle body and is the main part of the receptacle assembly 40 that is showing when the plug assembly 20 is connected to the receptacle assembly 40. Receptacle housing 46 also contains the magnetic shield which is necessary in order to reduce or eliminate external electromagnetic interference (EMI) from various other circuitry and wires present in the typical EP catheter lab environment or other hospital environment. The magnetic shield is preferably comprised of Mu metal although other type of know shielding may be used. Strain relief 54 assures a smooth transition between the receptacle housing 46 and the cable 15. This end manages the pigtail to connector interface.

The two-piece connector described above is designed to engage in only one way. This is achieved by visually lining up the different off-center and centered keys 29 on the plug assembly with the related key ways 51 on the receptacle assembly. These different off-center and entered keys and key ways are part of the plug body 26 and the receptacle body 48 respectively. After alignment the halves are pushed together until the plug assembly seats in the receptacle assembly and an audible click is heard which means that the lock and release button 28 has engaged the button catch feature 52. The two piece connector is now locked together. To disengage the user depresses the lock and release button away from the palm and the two halves are then unlocked.

The aforementioned components of the plug assembly may be made of numerous types of polymeric materials such as polycarbonate, polyurethane and other thermoplastic materials capable of use in injection molding.

Figure 3:
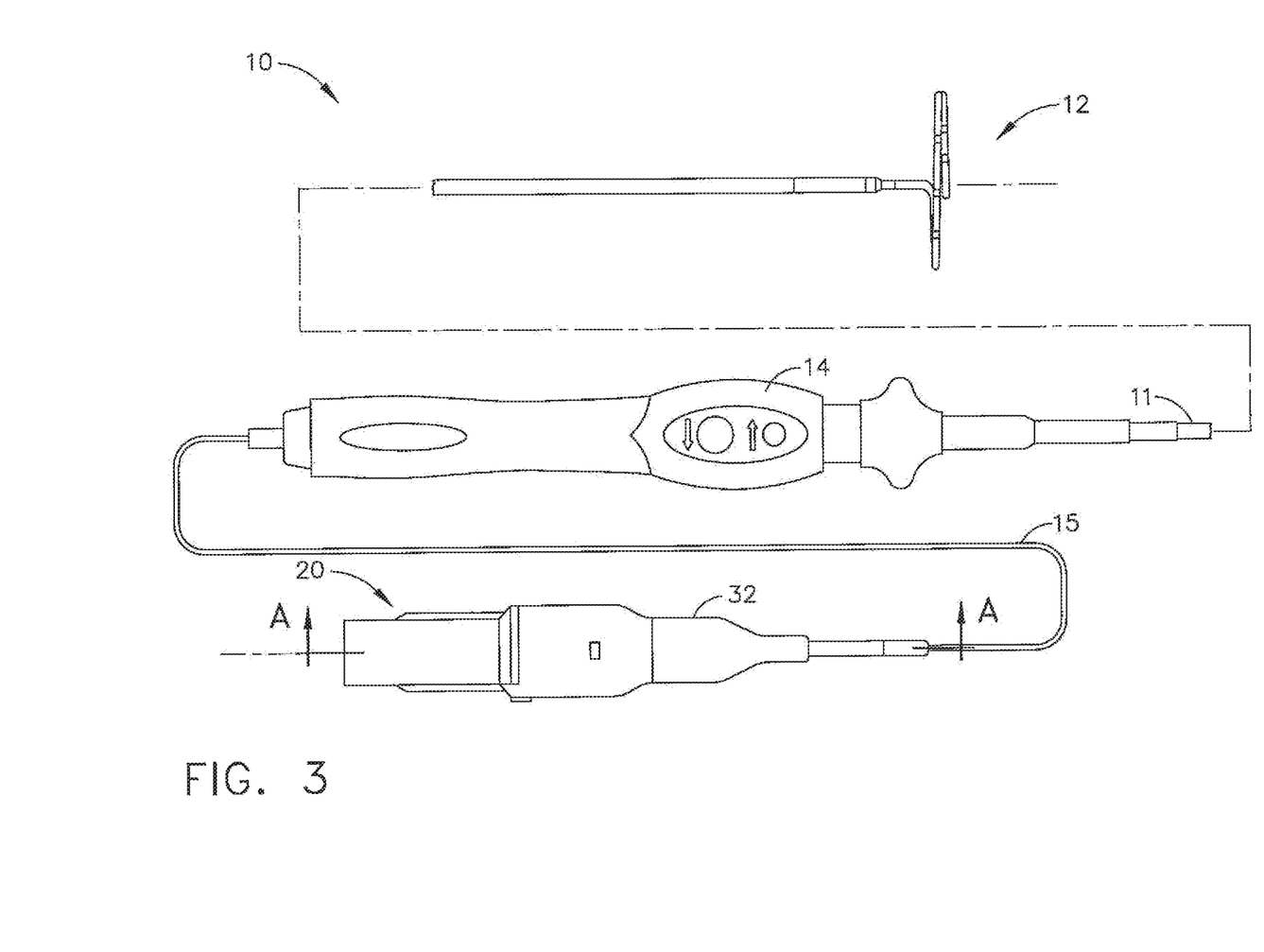
FIG. 3 is a plan view catheter attached to the plug assembly of the two-piece connector of the present invention.

FIG. 3 depicts a plan view of a catheter having the two piece connector of the present invention. Catheter has an elongated catheter body 11 which is disposed between the operator controlled handle 14 and distal tip 12 where the diagnostic and/or therapeutic electrodes are disposed. The catheter body 11 comprises an elongated tubular construction having a single, axial or central lumen. The catheter body is flexible, i.e., bendable, but substantially non-compressible along its length. The catheter body can be of any suitable construction and made of any suitable material. A presently preferred construction comprises an outer wall made of polyurethane or PEBAX. The outer wall may also comprise an imbedded braided mesh of stainless steel or the like to increase torsional stiffness of the catheter body so that, when the control handle is rotated, the intermediate section of the catheter will rotate in a corresponding manner.

The outer diameter of the catheter body is not critical, but is preferably no more than about 8 french, more preferably 7 french. Likewise the thickness of the outer wall is not critical, but is thin enough so that the central lumen can accommodate puller members (e.g., puller wires), lead wires, and any other desired wires, cables or tubing such as irrigation tubing. If desired, the inner surface of the outer wall is lined with a stiffening tube to provide improved torsional stability Components that extend between the control handle and the deflectable section pass through the central lumen of the catheter body. These components include lead wires for the tip dome electrode and ring electrodes proximal the tip dome electrode on the distal tip 12, an irrigation tubing for delivering fluid to the distal section (optional), a cable for a position location sensor carried in the distal section (optional), puller wire(s) for causing the proximal and distal deflections and a pair of thermocouple wires to sense temperature at the distal tip section.

At the distal end of the intermediate section is the distal tip section that includes the tip dome and the aforementioned plurality of lumens, nitinol tube, puller wires, electrically conductive wires to the tip and optional ring electrodes.

The electrodes are constructed of a biocompatible metal, including a biocompatible metal alloy. A suitable biocompatible metal alloy includes an alloy selected from stainless steel alloys, noble metal alloys and/or combinations thereof. In one embodiment, the tip electrode is a shell is constructed of an alloy comprising about 80% palladium and about 20% platinum by weight. In an alternate embodiment, the shell is constructed of an alloy comprising about 90% platinum and about % iridium by weight. The shell can formed by deep-drawing manufacturing process which produces a sufficiently thin but sturdy shell wall that is suitable for handling, transport through the patient's body, and tissue contact during mapping and ablation procedures. In a disclosed embodiment, the shell wall has a generally uniform thickness ranging between about 0.003 in and 0.010 in, preferably between about 0.003 in and 0.004 in, and more preferably about 0.0035 in. While the deep drawn method is well suited to manufacturing the shell with a sufficiently thin wall, it is understood that other methods, such as drilling and/or casting/molding, can also be used.

Control handle 14 is used by the operator to control the position of the catheter within the body of the patient. Control handle 14 may have disposed thereon various mechanism well known in the art for deflecting the distal tip 12 of the catheter or for varying the radius of a loop at the distal tip. In FIG. 3 the distal tip is depicted as having a loop structure, however, various distal tip structures are known and used in the art.

Electrical cable 15 connects the electrodes and biosensors (or other location sensing means) as well as any pressure sensing means to plug assembly 20 providing a pathway for electrical signals to travel from the distal tip through conductive leads in elongated catheter body 11 through handle 14 into plug assembly 20 into receptacle assembly 40 and ultimately to the electroanatomic and/ablation or other system.

Figure 4:
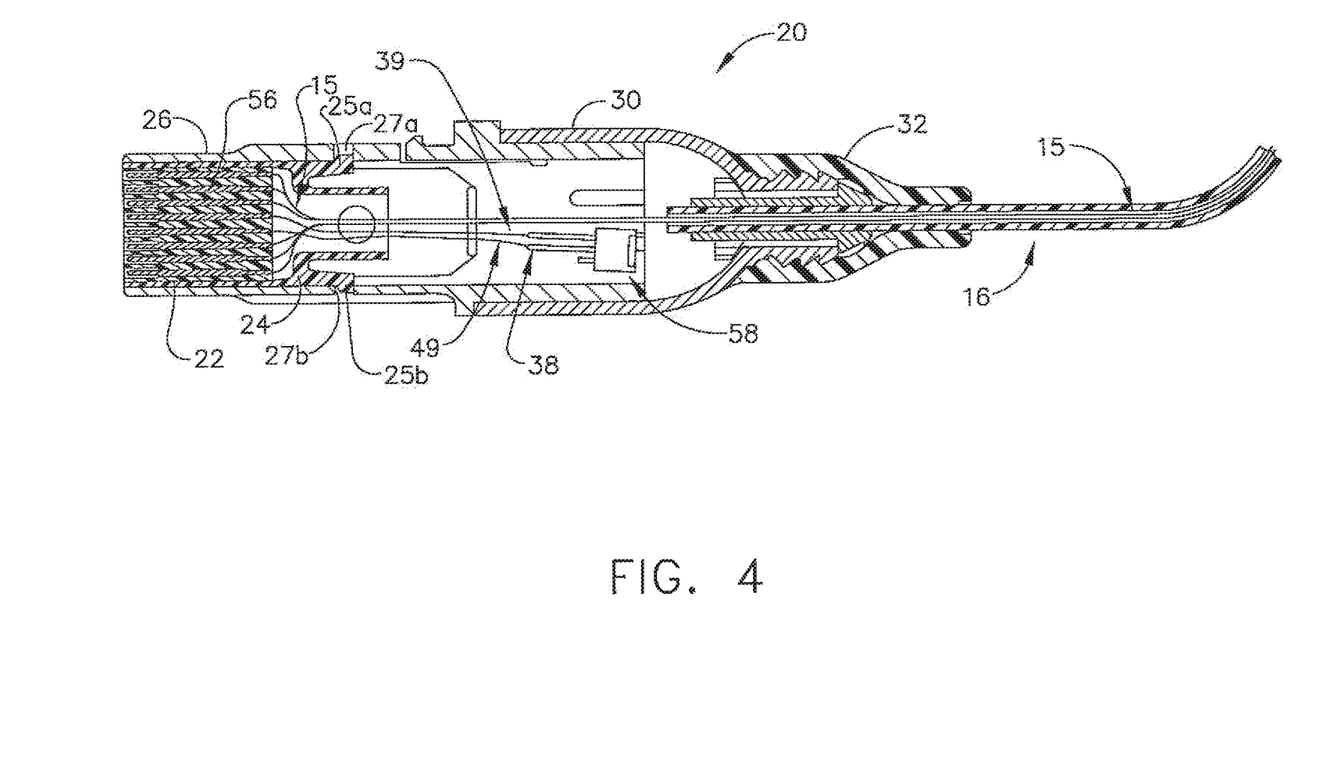
FIG. 4 is a cross-sectional view of the plug assembly of the FIG. 3 through lines A-A.

FIG. 4 is a cross-sectional depiction of the plug assembly 20 with associated wiring in an embodiment of the present catheter with two-piece connector. Electrical cabling 15 carrying the leads from the electrical elements in the distal tip as well as power from any ablation system to the ablation electrode in the distal tip enters strain relief 32 and the individual leads are connected to a plurality of pins 56 which are arranged in the plug insulator 22 of the plug assembly 20. An EEPROM 58 is placed in EEPROM recess 33 in plug body 26 depicted in FIG. 1. The EEPROM is used to store various catheter specific information such as biosensor calibration information, catheter identification information etc. Plug housing 30 functions as described above and is connected to plug body 26 through the snap features. Electrical leads 39 and 49 are connected to the EEPROM via solder connections 38 the EEPROM to two of pins 56 providing an electrical connection to receptacle assembly 40 and ultimately to a console for mapping and/or ablation. As can be seen any number of electrical leads may be connected to one or more pins 56 with the other end of such leads connected to various components such as an EEPROM, a PCB (if desired), diagnostic electrodes in the distal tip 12, ablation electrodes in the distal tip 12, magnetic position sensors (biosensors) in the distal tip 12, pressure sensing mechanisms in distal tip 12, micro-elements such as microelectrodes for recording intracardiac ECG, impedance measurements, microthermistors for temperature measurement, etc. The number of elements that may be connected is limited only by the number of pins 56.

Pins 56 in plug insulator 22 then provide an electrical connection to the mating connectors (not shown) in receptacle insulator 42. These mating connectors transfer the electrical sensor to electrical leads located in a cable (not shown) that then route the signals to a console that contains the control circuitry for the ablation and/or diagnostic procedure. A printed circuit board could also be disposed in the receptacle assembly 40 if it is desired to house certain of the electrical circuitry in a location not attached directly to the catheter.

An operator, such as an interventional cardiologist or electrophysiologist, inserts the catheter of the present invention through the vascular system of a patient so that a distal end of the catheter enters a chamber of the patient's heart. The operator advances the catheter so that the distal tip of the catheter engages endocardial tissue at a desired location or locations. The catheter is typically connected by a suitable connector at its proximal end to console. The console comprises a radio frequency (RF) generator, which supplies high-frequency electrical energy via the catheter for ablating tissue in the heart at the locations engaged by the distal tip, as described further hereinbelow. Alternatively, the catheter and system may be configured to perform ablation by other techniques that are known in the art, such as cryo-ablation, ultrasound ablation or ablation through the use of microwave energy.

Console may also use magnetic position sensing to determine position coordinates of distal end inside the heart of the patient. For this purpose, a driver circuit in console drives field generators to generate magnetic fields within the body of patient. Typically, the field generators comprise coils, which are placed below the patient's torso at known positions external to the patient. These coils generate magnetic fields in a predefined working volume that contains heart. A magnetic field sensor within distal end of catheter (shown in FIG. 2) generates electrical signals in response to these magnetic fields. A signal processor processes these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

A processor in the system typically comprises a general-purpose computer, with suitable front end and interface circuits for receiving signals from catheter and controlling the other components of console. The processor may be programmed in software to carry out the functions that are described herein. The software may be downloaded to console in electronic form, over a network, for example, or it may be provided on tangible media, such as optical, magnetic or electronic memory media. Alternatively, some or all of the functions of processor 36 may be carried out by dedicated or programmable digital hardware components. Based on the signals received from the catheter and other components of system, processor drives a display to give operator visual feedback regarding the position of distal end in the patient's body, as well as status information and guidance regarding the procedure that is in progress.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. In that regard, it can be understood that the order of the plug assembly and the receptacle assembly may be reversed in use, i.e., the receptacle assembly could be attached (fixedly or releasably) to the catheter handle 14 rather than the plug assembly. Additionally, the position of the snap features and receivers may be reveres as well as the lock and release button and lock catch. Furthermore, the EMI shielding could be placed in the receptacle body, the plug housing and/or the plug body rather than only in the receptacle housing.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter for use with a remote system for diagnosing or treating a patient, via a receptacle assembly having a proximal portion, a distal portion, and a button catch, the catheter comprising:
   a flexible elongated catheter body;
   a distal tip distal of the catheter body and having a plurality of electrodes;
   a control handle proximal of the catheter body;
   a plug assembly proximal of the control handle, the plug assembly having:
      a plug insulator having a plurality of contacts;
      an elongated plug body having a proximal portion and a distal portion, the proximal portion configured to receive the plug insulator;
      a plug insulator lead configured to secure the plug insulator in the proximal portion of the plug body;
      a plug housing configured to receive the distal portion of the plug body, the plug housing having a button; and
   a first cable extending between the control handle and the plug assembly, the first cable having a first plurality of electrical leads connected to the plurality of contacts;
   in which the plug insulator has a first key and a second key, the first and second keys having different sizes for one-way engagement between the plug insulator and the plug body,
   in which the proximal portion of the plug body is configured to be received in the distal portion of the receptacle assembly, and
   in which the button is configured to releasably engage with the button catch.

2. A medical system comprising:
   the catheter of claim 1; and
   the receptacle assembly, in which the receptacle assembly further comprises:
   a receptacle insulator having second plurality of contacts;
   a receptacle body having a proximal portion and a distal portion, the proximal portion configured to receive the receptacle insulator, and the distal portion configured to receive the proximal portion of the plug body;
   a receptacle insulator lead configured to secure the receptacle insulator in the proximal portion of the receptacle body;
   a receptacle housing configured to receive the receptacle body; and
   and a second cable extending proximally from the receptacle assembly, the second cable having a second plurality of electrical leads connected to the second plurality of contacts.

3. The catheter of claim 1, in which each of the first plurality of electrical leads pass through the catheter body, through the control handle, and into the plug assembly.

4. The catheter of claim 3, in which each of the first plurality of electrical leads are connected to a respective electrode of the distal tip.

5. The medical system of claim 2, in which the second cable is further connected to the remote system.

6. The medical system of claim 2, further comprising electronic circuitry for converting signals from the plurality of electrodes into digital signals.

7. The medical system of claim 2, in which the first and second plurality of electrical leads are connected.

8. The medical system of claim 2, in which a proximal portion of the plug body comprises a third key and the receptacle body has a key way, the third key and key way configured for one-way engagement.

9. The catheter of claim 1, in which the plug body comprises an EEPROM recess configured to secure an EEPROM therein.

10. The catheter of claim 1, in which the plug assembly further comprises a strain relief configured to provide an atraumatic transition between the plug housing and the first cable.

11. The catheter of claim 1, in which the first plurality of contacts comprise pins.

12. The catheter of claim 1 in which the first plurality of contacts comprise socket contacts.

13. The medical system of claim 2, in which the receptacle housing comprises a shielding configured to reduce electromagnetic interference.

14. The medical system of claim 13, in which the shielding comprises a layer of Mu metal disposed on an inside surface of the receptacle housing.

15. The medical system of claim 2, in which the receptacle assembly further comprises a strain relief configured to provide an atraumatic transition between the receptacle housing and the second cable.

16. The medical system of claim 2, in which the receptacle insulator has a third key and a fourth key, the third and fourth keys configured for one-way engagement between the receptacle insulator and the receptacle housing.

17. The catheter of claim 1, in which the plug body comprises a plurality of snap features, and the plug housing comprises a plurality of snap receivers.

* * * * *